(12) United States Patent
Kroll

(10) Patent No.: US 8,551,019 B1
(45) Date of Patent: Oct. 8, 2013

(54) VARIABLE STIFFNESS GUIDE WIRE

(75) Inventor: Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 1403 days.

(21) Appl. No.: 11/470,546

(22) Filed: Sep. 6, 2006

(51) Int. Cl.
*A61B 5/00* (2006.01)

(52) U.S. Cl.
USPC ............................................... 600/585

(58) Field of Classification Search
USPC ............................................... 600/585
See application file for complete search history.

(56) References Cited

U.S. PATENT DOCUMENTS

| | | | |
|---|---|---|---|
| 4,758,222 A | 7/1988 | McCoy | |
| 5,211,183 A | 5/1993 | Wilson | |
| 5,389,072 A * | 2/1995 | Imran | 604/95.05 |
| 5,497,784 A * | 3/1996 | Imran | 600/585 |
| 5,800,497 A | 9/1998 | Bakels et al. | |
| 5,860,914 A * | 1/1999 | Chiba et al. | 600/151 |
| 6,672,338 B1 * | 1/2004 | Esashi et al. | 138/119 |
| 2003/0097080 A1 * | 5/2003 | Esashi et al. | 600/585 |
| 2004/0054322 A1 * | 3/2004 | Vargas | 604/95.04 |
| 2005/0027244 A1 | 2/2005 | Eidenschink | |

FOREIGN PATENT DOCUMENTS

WO    0200287 A1    1/2002

* cited by examiner

*Primary Examiner* — Max Hindenburg
*Assistant Examiner* — Renee Danega

(57) ABSTRACT

A guide wire is heated by application of electricity to change the stiffness of at least a portion of the guide wire. That portion of the guide wire may thus be selectively softened wherever that portion needs to be bent to facilitate routing the guide wire through curves or obstacles in a desired path.

18 Claims, 6 Drawing Sheets

VARIABLE STIFFNESS GUIDE WIRE

TECHNICAL FIELD

This application relates generally to a guide wire and, more specifically, to a guide wire having variable stiffness.

BACKGROUND

A guide wire may be used to route a component through a passageway to a location that may be otherwise relatively inaccessible. For example, a physician may use a guide wire to implant a cardiac lead in a patient's heart. Here, the guide wire may be initially inserted into a vein of the patient then routed through the vein to the heart. In some applications the lead may then be routed over the guide wire for implantation.

In general, a guide wire must be sufficiently rigid so that it may be pushed through a desired path yet be sufficiently flexible to enable it to navigate bends and obstacles in the path. In the example of a guide wire for implanting a cardiac lead, the guide wire must be sufficiently stiff to enable a physician to advance the guide wire through the vein (and potentially through tissue) by pushing on a proximal end of the guide wire. In addition, the guide wire needs to be sufficiently flexible to navigate various bends in the vein as the guide wire is directed toward the heart.

SUMMARY

A summary of various aspects and/or embodiments of an apparatus constructed or a method practiced according to the invention follows. For convenience, one or more embodiments of an apparatus constructed or a method practiced according to the invention may be referred to herein simply as an "embodiment."

In one embodiment at least a portion of a guide wire is heated to change the stiffness of the guide wire. For example, a current may be passed through a portion of the guide wire to alter the stiffness of the portion. The portion may have sufficient resistance such that it heats up upon introduction of a given amount of current. Through appropriate placement of the portion in the guide wire and selective application of appropriate levels of current flow, the portion may be softened to a desired degree whenever the portion needs to bend to efficiently traverse a bend or other feature of the path.

In one embodiment a distal end of the guide wire is softened by heating. The guide wire has sufficient stiffness such that it may be pushed at its proximal end yet is configurable so that the leading end of the guide wire may be softened when necessary to enable the leading end of the guide wire to effectively navigate bends or obstacles in the path.

BRIEF DESCRIPTION OF THE DRAWINGS

These and other features, aspects and advantages of the invention will be more fully understood when considered with respect to the following detailed description, appended claims and accompanying drawings, wherein:

FIG. 2, including

Figure 1:
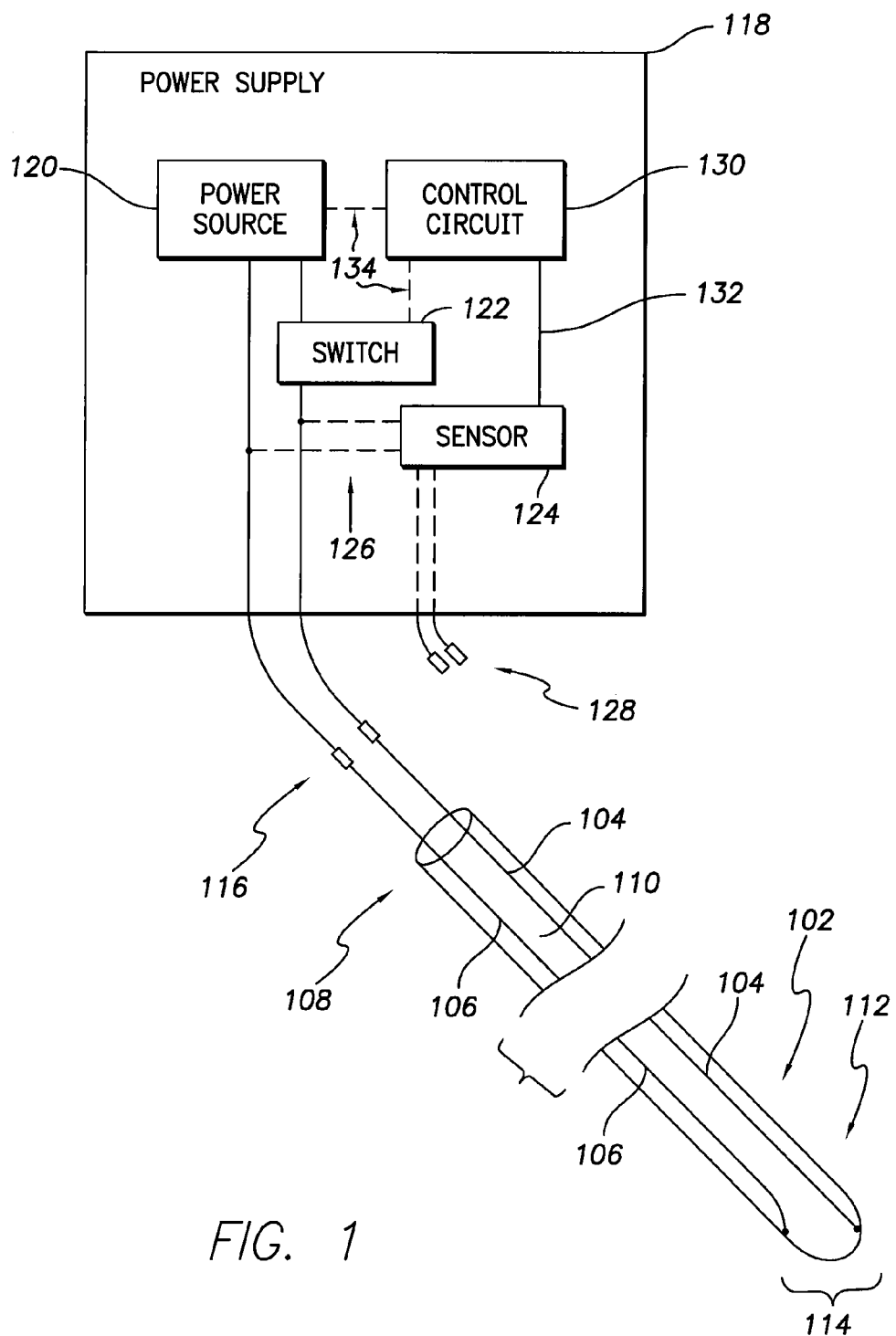
FIG. 1 is a simplified diagram of one embodiment of a guide wire assembly constructed in accordance with the invention.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and/or functional details disclosed herein are merely representative and do not limit the scope of the invention.

For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s).

FIG. 1 illustrates one embodiment of a guide wire assembly including a guide wire 102. To improve the clarity of FIG. 1, the relative sizes of some of the components shown have been modified and the central portion of the guide wire 102 has been cut away. Two insulated electrical conductors 104 and 106 run from a proximal end 108 of the guide wire 102 through an interior space 110 to a distal end 112 of the guide wire 102. The conductors 104 and 106 attach to the distal end 112 of the guide wire 102 across a conductive portion 114 through which current flow may be induced. Connectors 116 attached to the proximal end of the conductors 104 and 106 enable a power supply 118 to connect to the conductors 104 and 106.

In one embodiment the power supply 118 includes a power source 120 and a switch 122 for controlling the amount of current that flows through the conductors 104 and 106. The power supply 118 may incorporate various types of switches to control the current flow. For example, the switch 122 may be an on-off type switch, a switch having variable resistance such as a potentiometer or a switch with discrete resistance settings, etc. The power source 120 may supply a direct current or an alternating current having any given waveform. In some embodiments the power source 120 may include a battery and, if applicable, associated converter circuitry. For example, direct current from the battery may be chopped and fed through a high current transformer to deliver a high current, low voltage signal to the portion 114.

When the guide wire 102 is inserted into a passage (e.g., a vein), an operator performing the installation may control the stiffness of the portion 114 by controlling the current flow through the portion 114. For example, the operator may adjust the switch 122 to increase the current flow. The increase in current flow may cause the portion 114 to heat up which, in turn, may reduce the stiffness of the portion 114. The portion 114 may thus have a continuously variable stiffness that is varied by controlling the amount of power delivered to the portion 114.

The power supply 118 also may include one or more sensors (hereafter referred to as "sensor 124") that may be used to determine the actual or approximate flexibility of the portion 114. The sensor 124 may provide feedback (e.g., output data, a display readout, etc.) to another component or the operator indicative of the flexibility of the portion 114. As a result, the operator may control the power supply 118 (e.g., via the switch 122) to obtain a desired level of stiffness for the portion 114. In one embodiment the sensor 124 may determine or estimate the resistance of the portion 114. For example, the sensor 124 may sense (e.g., via optional leads represented by dashed lines 126) the magnitude of or change in current flow through the portion 114.

In one embodiment an operator may use the sensor 124 to measure the temperature at the portion 114. For example, the operator may monitor the temperature of the portion 114 to ensure that the temperature does not exceed a level that may damage surrounding tissue (e.g., greater than 55° C. for heart cells). Alternatively, the temperature of the portion 114 may be used to indirectly determine or estimate the stiffness of the portion 114. The sensor 124 may thus comprise a temperature sensor circuit that connects via conductors (e.g., as represented by dashed lines 128) routed through the guide wire 102 to a temperature sensing component such as a thermocouple (not shown) that is provided in the guide wire 102 at or near the portion 114.

In one embodiment a control circuit 130 in or associated with the power supply may process a signal 132 from the sensor 124 to automatically control (e.g., via control lines as represented by dashed lines 134) the current provided to the portion 114. For example, if the detected temperature, current flow or softness of the portion 114 exceeds (or a detected resistance is below) a threshold or if a measured change in such parameters is deemed excessive in comparison to, for example, an expected range, the power supply 118 may automatically reduce or cut off the current flow through the portion 114. In this way, the control circuit 130 may reduce the risk that heat emanating from the portion 114 will damage (e.g., coagulate) surrounding blood or damage (e.g., ablate) adjacent tissue.

In one embodiment the guide wire 102 may include several conductive portions (not shown). In this case, the guide wire 102 may include at least one individual conductor for each conductive portion and the power supply 118 may include several switches, etc., for selectively controlling current flow to the each of the conductive portions.

The conductive portion 114 and/or the guide wire 102 may be constructed of a variety of materials including, for example, stainless steel, monel, beryllium, titanium or a conductive polymer. When the guide wire 102 is used in a medical application (e.g., inserted into a patient) the guide wire may be constructed of a biocompatible material. In some embodiments the guide wire 102 may be constructed of a material that is stiffer than normal. Here, since the guide wire 102 may be configured to more easily traverse sharp bends, the entire guide wire 102 need not be as flexible as a guide wire that is not configurable.

The conductive portion 114 may be a portion of the guide wire 102 or may be a separate material that is, for example, attached to or formed with the guide wire 102. In one embodiment the guide wire 102 may consist of a coiled spring. In this case, the current may flow through all or a portion of the coiled spring. The portion 114 may thus comprise a different material, a coiled spring having a smaller cross section (e.g., as discussed below) or some other structure that causes the portion 114 to heat when subjected to the current.

In one embodiment the resistances of the conductors 104 and 106 are substantially lower than the resistance of the conductive portion 114. For example, the conductors 104 and 106 may be constructed of a material such as silver. As a result, virtually all the resistive load of the circuit (and accompanying dissipative heating) is in the conductive portion 114.

The shape and dimensions of the guide wire 102 and conductive portion 114 will depend on the particular needs of the application. As an example, in one embodiment where the guide wire is used to implant a cardiac lead the guide wire 102 may have an elongated, tubular shape (e.g., a tube or substantially a tube or similar shape) and the conductive portion 114 may have a length on the order of 5 millimeters and an outer diameter on the order of 1 millimeter or less. It should be appreciated that other shapes and dimensions may be used in this or other applications.

Figure 2A:
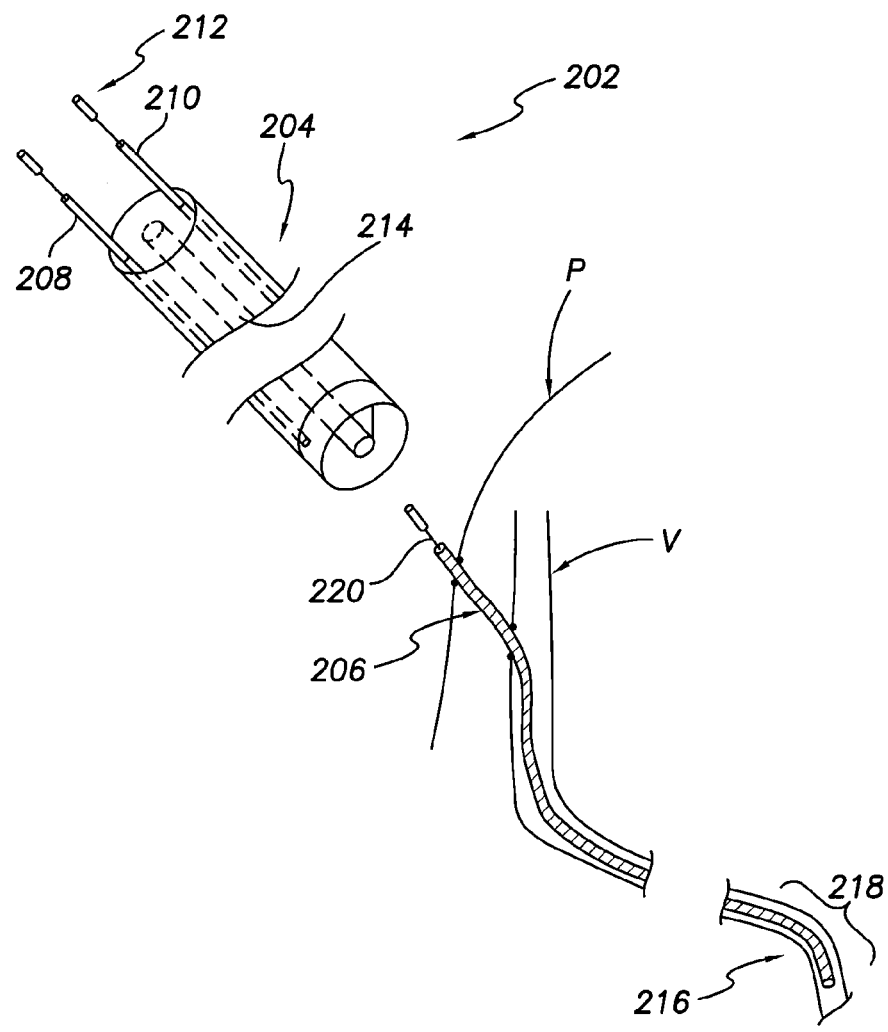
FIGS. 2A and 2B, is a simplified diagram of one embodiment of a lead assembly including a guide wire constructed in accordance with the invention.
Figure 2B:
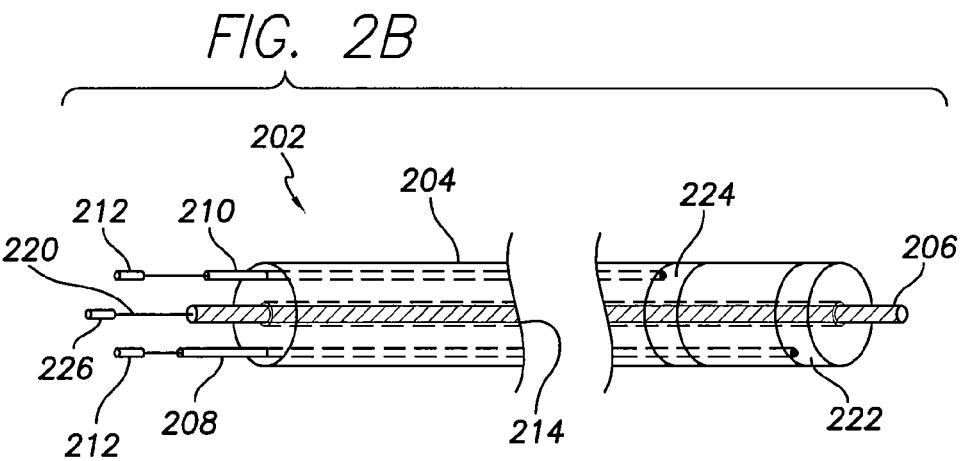

FIG. 2, including FIGS. 2A and 2B, illustrates one embodiment of a lead assembly 202 including a lead 204 and a guide wire 206. FIG. 2A relates to the initial insertion of the guide wire 206 into a vein V of a patient P. FIG. 2B relates to the subsequent placement of the lead 204 over the guide wire 206. To improve the clarity of FIG. 2, the relative sizes of some of the components and patient features shown have been modified and central portions of the lead 204 and guide wire 206 have been cut away.

The lead 204 may include several lumens through which one or more conductors (e.g., conductors 208 and 210) are routed or a fluid is dispensed (not shown). A connector 212 may be attached to the proximal end of each conductor 208 and 210. At their distal ends, the conductors 208 and 210 may connect to, for example, a tip electrode 222 and a ring electrode 224, respectively (FIG. 2B). The lead 204 also may define a lumen 214 for routing the lead 204 over the guide wire 206.

Referring to FIG. 2A, in a typical application the guide wire 206 is initially routed through an implant ingress site (e.g., a hole in the vein V). To more easily traverse a bend or obstacle 216 along the desired path, the operator may temporarily reduce the stiffness of a controllable portion 218 (e.g., the leading end) of the guide wire 206. As discussed above, this may be accomplished by providing a current to the controllable portion 218 via one or more conductors 220 in the guide wire 206. Here, once the controllable portion 218 of the guide wire 206 passes the bend or obstacle 216, the operator may increase the stiffness of the controllable portion 218. The operator may increase the stiffness by, for example, reducing or terminating current flow to the controllable portion 218. Here, after the controllable portion 218 is straightened or allowed to straighten, the controllable portion 216 may be stiffened so that it will more effectively traverse straighter sections of the upcoming path.

Referring now to FIG. 2B, after the operator moves the guide wire 206 to a desired position the operator may install the lead 204 over the guide wire 206. That is, the lumen 214 of the lead 204 is passed over the guide wire 206 and its associated components. Here, the operator may initially run the lead 204 over any connector(s) 226 for any conductor(s) 220 protruding from the proximal end of the guide wire 206. The operator may then run the lead 204 over the proximal end of the guide wire 206 and continue feeding the lead 204 over the guide wire 206 until the lead 204 is placed at a desired implant position.

Figure 3:
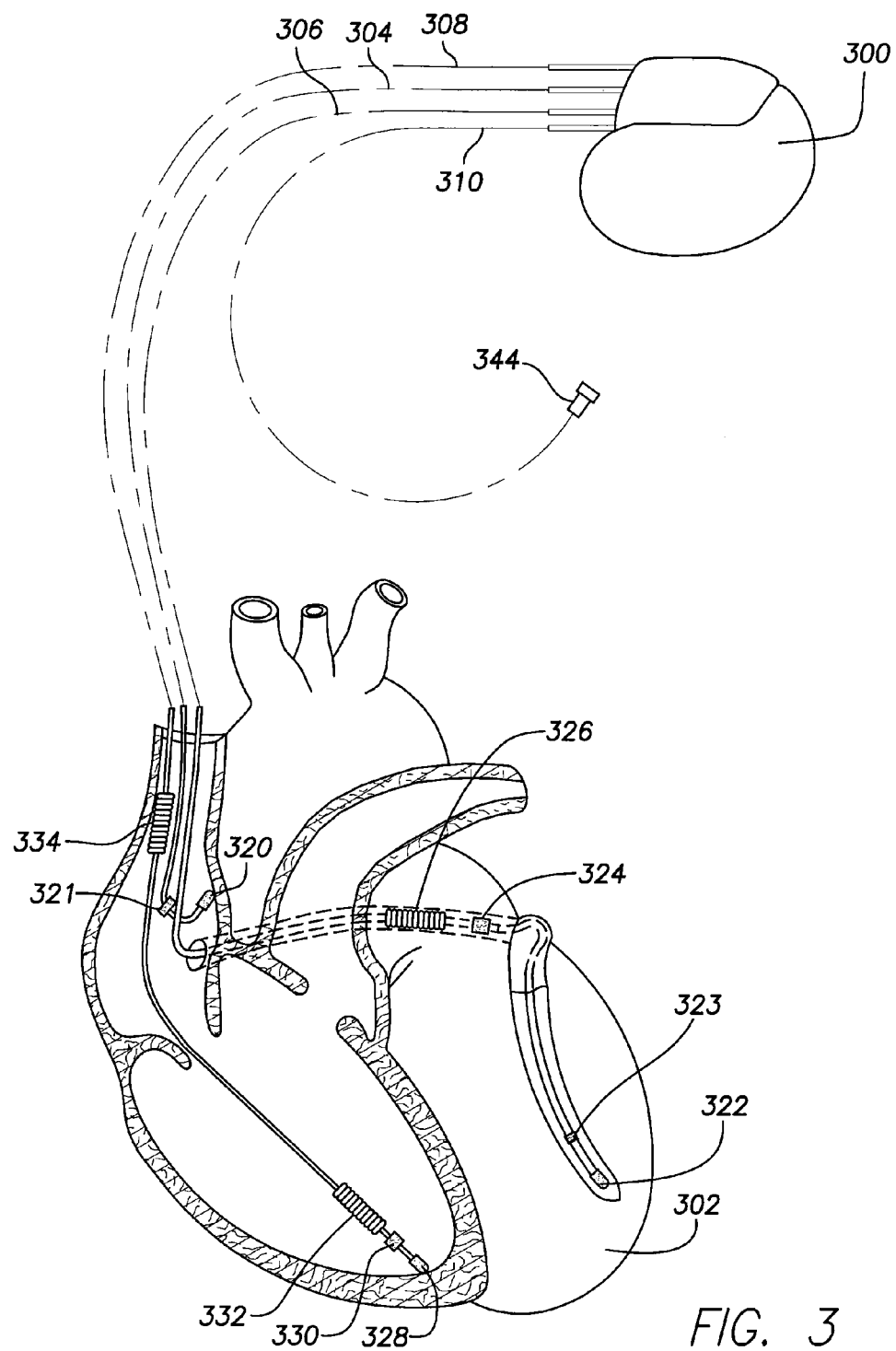
FIG. 3 is a simplified diagram of one embodiment of an implantable stimulation device in electrical communication with at least three leads implanted in a patient's heart for delivering multi-chamber stimulation and shock therapy in accordance with the invention.

Referring now to FIG. 3, in one embodiment a guide wire may be used to implant one or more cardiac leads for an implantable cardiac device (e.g., a stimulation device). It is to be appreciated and understood that a guide wire may be used in conjunction with other devices and that the description below is given, in its specific context, to assist the reader in understanding, with more clarity, the inventive embodiments described herein.

FIG. 3 shows an exemplary implantable cardiac device 300 in electrical communication with a patient's heart 302 by way of three leads 304, 306, and 308, suitable for delivering multi-chamber stimulation and shock therapy, that may be implanted using a guide wire as taught herein. To sense atrial cardiac signals and to provide right atrial chamber stimulation therapy, device 300 is coupled to an implantable right atrial lead 304 having, for example, an atrial tip electrode 320, which typically is implanted in the patient's right atrial appendage or septum. FIG. 3 shows the right atrial lead 304 as having an optional atrial ring electrode 321.

To sense left atrial and ventricular cardiac signals and to provide left chamber pacing therapy, device 300 is coupled to a coronary sinus lead 306 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 306 is designed to receive atrial and ventricular cardiac signals and to deliver left ventricular pacing therapy using, for example, a left ventricular tip electrode 322 and, optionally, a left ventricular ring electrode 323; provide left atrial pacing therapy using, for example, a left atrial ring electrode 324; and provide shocking therapy using, for example, a left atrial coil electrode 326 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

Device 300 is also shown in electrical communication with the patient's heart 302 by way of an implantable right ventricular lead 308 having, in this implementation, a right ventricular tip electrode 328, a right ventricular ring electrode 330, a right ventricular (RV) coil electrode 332 (or other electrode capable of delivering a shock), and superior vena cava (SVC) coil electrode 334 (or other electrode capable of delivering a shock). Typically, the right ventricular lead 308 is transvenously inserted into the heart 302 to place the right ventricular tip electrode 328 in the right ventricular apex so that the RV coil electrode 332 will be positioned in the right ventricle and the SVC coil electrode 334 will be positioned in the superior vena cava. Accordingly, the right ventricular lead 308 is capable of sensing or receiving cardiac signals, and delivering stimulation in the form of pacing and shock therapy to the right ventricle.

Device 300 is also shown in electrical communication with a lead 310 including one or more components 344 such as a physiologic sensor. The lead 310 may be positioned in, near or remote from the heart.

It should be appreciated that the device 300 may connect to leads other than those specifically shown. In addition, the leads connected to the device 300 may include components other than those specifically shown. For example, a lead may include other types of electrodes, sensors or devices that serve to otherwise interact with a patient or the surroundings.

Figure 4:
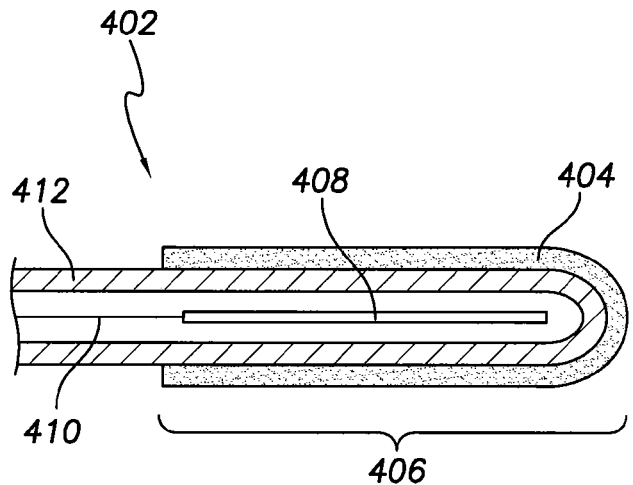
FIG. 4 is a simplified diagram of one embodiment of a guide wire constructed in accordance with the invention.

FIG. 4 illustrates one embodiment of a guide wire 402 that includes an insulator 404. The insulator 404 may be used, for example, to prevent surrounding matter (e.g., bodily tissue or fluid such as blood) from unduly cooling a heated portion 406 of the guide wire 402 and/or to reduce the risk of heat from the heated portion 406 from damaging surrounding matter (e.g., coagulating blood or ablating tissue). The insulator 404 may surround at least a portion of the heated portion 406 and, optionally, other (e.g., adjacent) portions of the guide wire. Depending on the particular application, the insulator 404 may be constructed of a variety of materials and may be incorporated into the guide wire 402 in a variety of ways. For example, the insulator 404 may be made of parylene, polysulfane, a polymer or other materials. The insulator 404 may be incorporated into the guide wire 402 by depositing an insulator material on the guide wire 402, adhering an insulator material to the guide wire 402, physically interlocking these components or through the use of other techniques.

FIG. 4 also illustrates an embodiment including one or more heating elements (hereafter referred to as heating element 408) for heating the portion 406 of the guide wire 402. In this embodiment the heating element 408 is located at or near the portion 406 and connects to a power supply (not shown) via one or more conductors 410 and/or the guide wire 402 (in an embodiment where the main body 412 of the guide wire 402 is conductive). The heating element 408 may include one or more resistive elements including, for example, coiled wires.

Figure 5:
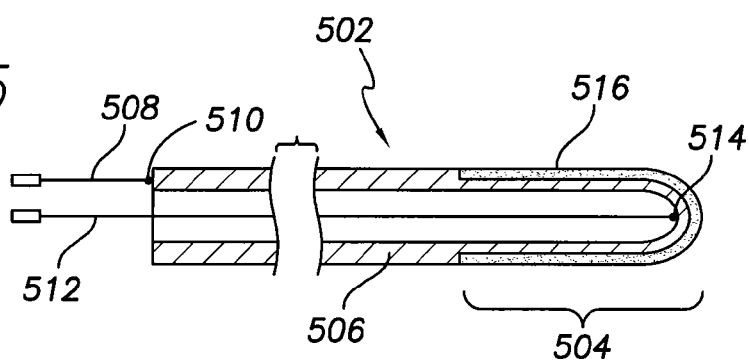
FIG. 5 is a simplified diagram of one embodiment of a guide wire constructed in accordance with the invention.

FIG. 5 illustrates one embodiment of a conductive guide wire 502 where the main body 506 of the guide wire 502 has a reduced thickness (e.g., cross section) in a portion 504 of the guide wire where stiffness is controllable. In this case, the portion 504 will have a higher resistance than the rest of the guide wire due to the reduced thickness of the portion 504. Here, one conductor 508 connected to the power supply connects to a proximal end of the guide wire (e.g., at connection point 510) while another conductor 512 connects to a distal end of portion 504 (e.g., at connection point 514). Consequently, upon application of an appropriate current the portion 504 may be subject to a significantly greater rise in temperature than the remainder of the guide wire 502.

FIG. 5 also shows an embodiment where an external surface of an insulator 516 may be co-circumferential with an external surface of the body of the guide wire 502. Accordingly, an insulator 516 may be incorporated into the guide wire 502 without significantly affecting the maneuverability of the guide wire 502.

Figure 6:
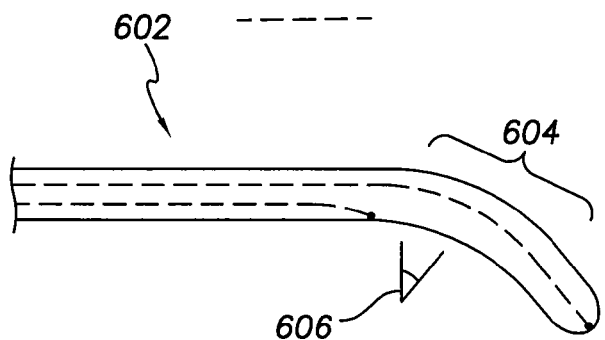
FIG. 6 is a simplified diagram of one embodiment of a guide wire constructed in accordance with the invention.

Referring now to FIG. 6, in some embodiments it may be desirable to configure a guide wire 602 with a predisposition to bend in a selected direction. For example, a bent portion 604 at the distal end of the guide wire 602 may have a bend with a radius 606 on the order of 30 degrees or some other value. Such a configuration may make it easier to route the guide wire 602 through bends or around obstacles. As discussed herein, the predisposed bent portion 604 of the guide wire 602 or any other portion of the guide wire 602 may be configured to have variable stiffness. Thus, the bent portion 604 may be heated to enable the portion 604 to be straightened at least in part when traversing a relatively straight section of a path or to enable the portion 604 to bend to a greater degree when traversing a significant bend in the path. When cooled, the portion 604 may substantially return to its original bent configuration. Accordingly, an operator may selectively adjust the stiffness of the portion 604 to facilitate routing the guide wire 602 through a path.

Figure 7:
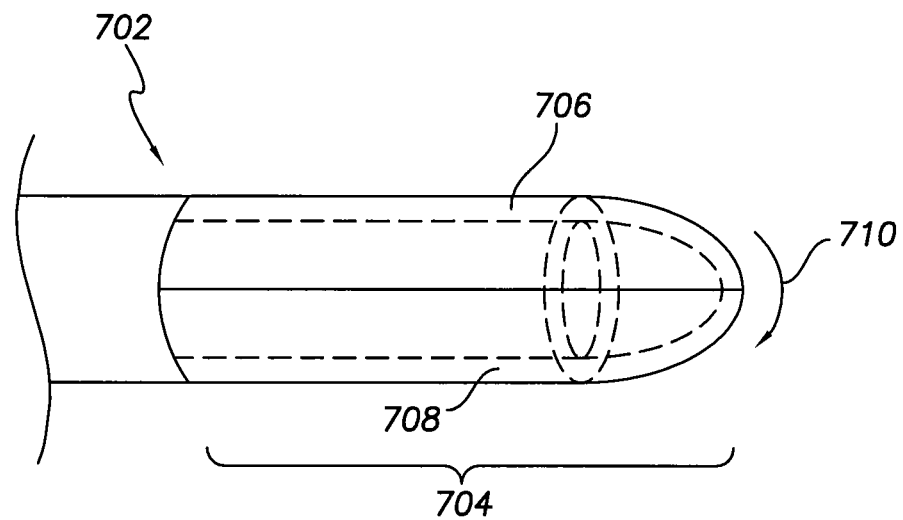
FIG. 7 is a simplified diagram of one embodiment of a guide wire constructed in accordance with the invention.

FIG. 7 illustrates one embodiment of a guide wire 702 that includes a portion 704 that bends in a predisposed manner when heated. In some embodiments the portion is constructed of different materials (e.g., materials 706 and 708). For example, the portion 704 may include different metals, a bimetallic compound, etc., where the different materials have different coefficients of thermal expansion. As a result, when the materials are heated (e.g., upon application of a current or radiated heat) they may bend in a predefined manner (e.g., in the direction of arrow 710).

Also as discussed herein, application of heat may affect the stiffness of these materials. Thus, the portion 704 may be heated even more to enable the portion 704 to bend to a greater degree when traversing a sharp bend in the path. When cooled, the portion 704 may substantially return to its original configuration. Accordingly, an operator may selectively adjust the stiffness of the portion 704 to facilitate routing of the guide wire 702 through a path.

Figure 8:
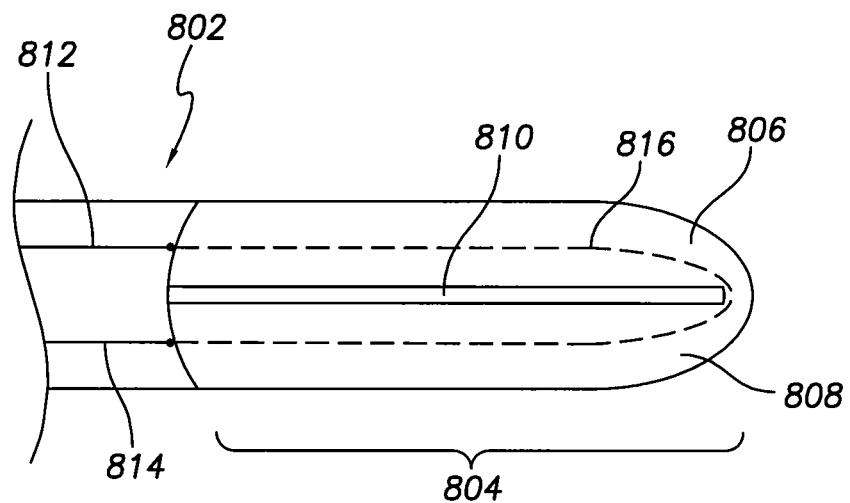
FIG. 8 is a simplified diagram of one embodiment of a guide wire constructed in accordance with the invention.

FIG. 8 illustrates one embodiment of a guide wire 802 where a portion 804 that is heated is constructed of two or more sections (e.g., sections 806 and 808). These different sections may comprise, for example, similar materials or different materials as discussed above in conjunction with FIG. 7. In some embodiments the sections 806 and 808 may be separated at least in part by one or more insulators 810. In the example of FIG. 8, a conductor 812, 814 is attached to each section 806, 808, respectively, at a proximal end of the portion 804. Current flow may thus be established through the portion 804 as represented by the dashed line 816.

Figure 9:
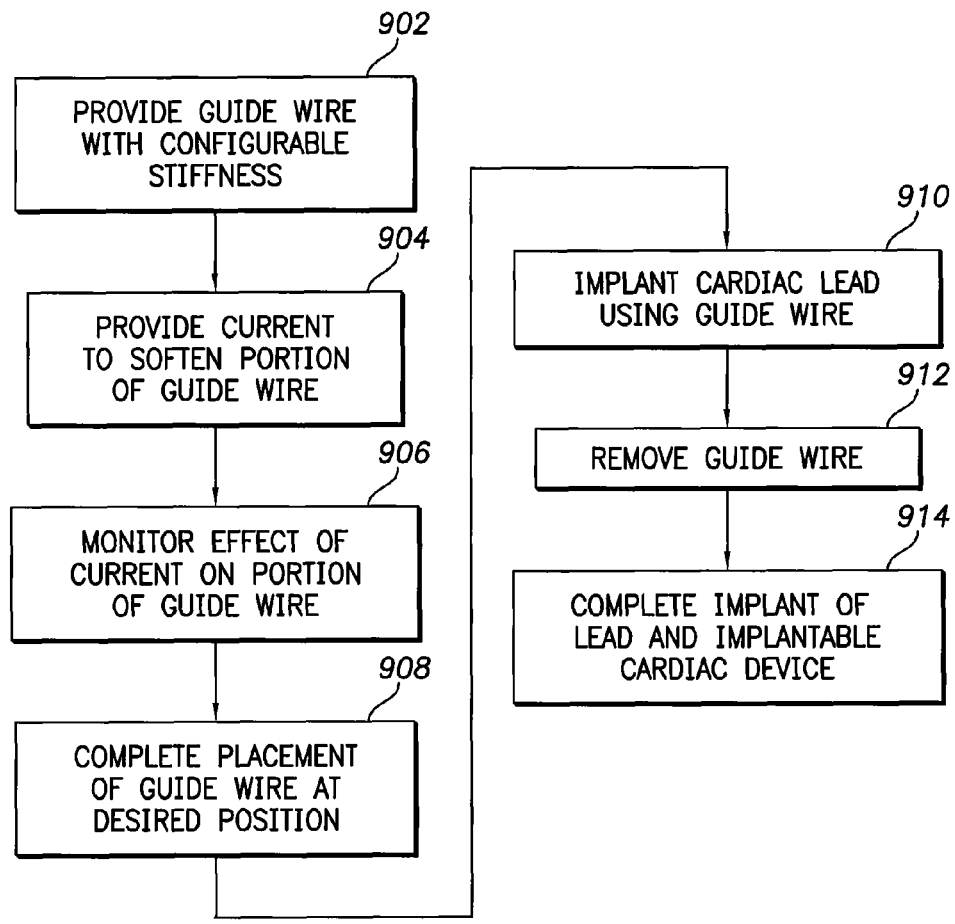
FIG. 9 is a flow chart of one embodiment of operations that may be performed in accordance with the invention.

Referring now to FIG. 9 one embodiment of lead implant operations that may be performed in conjunction with a guide wire as taught herein will be discussed. Initially, as represented by block 902, an operator inserts a guide wire having a configurable stiffness into an entry site (e.g., an opening in a vein).

When the guide wire encounters a bend or obstacle, the operator causes current to flow through a portion of the lead to heat and thereby soften that portion of the lead (block 904). As a result, the heated portion of the lead may bend or otherwise change its configuration to more easily pass the bend or obstacle.

As represented by block 906, the operator or a device associated with the guide wire may monitor the effects of the current on the heated portion. For example, as discussed above, a sensor in the guide wire or an external sensor may be used to monitor stiffness, temperature, current flow, resistance or other parameters. In response to the sensed signal the operator or device may modify the current flow or some other aspect of the procedure (e.g., the rate at which the guide wire is being inserted).

The procedure at blocks 904 and 906 may be repeated as necessary to route the guide wire past various bends or obstacles along the desired path. Ultimately, the guide wire is placed at the desired position (block 908).

As represented by block 910, the operator may then implant a cardiac lead using the guide wire. For example, in an over-the-wire procedure, a lumen in the lead may be used to route the lead over the guide wire.

Once the lead is implanted, the guide wire may be removed (block 912). The cardiac lead may then be connected to the implantable cardiac device 300 (block 914).

It should be appreciated that the embodiments described above illustrate but a few examples of mechanisms that may be used to implement the teachings herein and that other mechanisms may be used in this regard. For example, other mechanisms may be employed to generate and provide power to at least a portion of the guide wire. Other mechanisms may be used to provide feedback regarding the stiffness or approximate stiffness of at least a portion of the guide wire. Other mechanism may be employed to heat at least a portion of the guide wire. The guide wire and related components may be constructed of materials other than those shown.

In summary, the invention described herein generally relates to improved lead and guide wire assemblies. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A guide wire comprising:
   an elongated tubular member having an electrically conductive portion, the electrically conductive portion thermally softening in response to a current flow through the electrically conductive portion; and
   at least one conductor, coupled to the electrically conductive portion through the elongated tubular member, for providing the current to resistively heat the electrically conductive portion.

2. The guide wire of claim 1 wherein the electrically conductive portion is at a distal end of the elongated tubular member.

3. The guide wire of claim 1 wherein the electrically conductive portion has a variable stiffness that is controllable in accordance with magnitude of the current flow.

4. The guide wire of claim 1 comprising an insulator covering at least a portion of the electrically conductive portion.

5. The guide wire of claim 1 wherein the at least one conductor comprises two conductors attached at opposite ends of the electrically conductive portion.

6. The guide wire of claim 1 wherein the electrically conductive portion has a predefined bend.

7. The guide wire of claim 1 wherein the electrically conductive portion is configured to automatically bend upon application of the current.

8. The guide wire of claim 1 wherein the electrically conductive portion is a conductive polymer.

9. A guide wire assembly comprising:
   a power supply for generating a current;
   an elongated tubular member having an electrically conductive portion, the electrically conductive portion thermally softening when the current flows through the electrically conductive portion; and
   at least one conductor, coupled to the electrically conductive portion and adapted to be coupled to the power supply, for providing the current to resistively heat the electrically conductive portion.

10. The guide wire assembly of claim 9 comprising a switch for controlling the flow of the current from the power supply to the electrically conductive portion.

11. The guide wire assembly of claim 9 comprising a variable resistor for controlling the flow of the current from the power supply to the electrically conductive portion.

12. The guide wire assembly of claim 9 wherein the current flow is varied over a continuous range to impart a continuous range of variable stiffness on the electrically conductive portion.

13. The guide wire assembly of claim 9 wherein the current flow is incremented over a range to impart incremental degrees of stiffness on the electrically conductive portion.

14. The guide wire assembly of claim 9 comprising a sensor for sensing an effect on the electrically conductive portion resulting from the current flow through the electrically conductive portion.

15. The guide wire assembly of claim 14 comprising a control circuit for automatically adjusting the current flow in accordance with the effect.

16. The guide wire assembly of claim 9 wherein the power supply generates an alternating current signal.

17. The guide wire assembly of claim 9 wherein the power supply generates a direct current signal.

18. The guide wire assembly of claim 9 wherein the electrically conductive portion is a conductive polymer.

\* \* \* \* \*